United States Patent
Lee et al.

(10) Patent No.: US 7,857,285 B2
(45) Date of Patent: Dec. 28, 2010

(54) LUBRICIOUS OR/AND WETTABLE OR/AND ANTI-THROMBIN ELASTOMERIC GLAND MATERIALS IN LUER ACTIVATED DEVICES

(75) Inventors: Yann-Per Lee, Vernon Hills, IL (US); Vince Desecki, Spring Grove, IL (US)

(73) Assignees: Baxter International Inc., Deerfield, IL (US); Baxter Healthcare S.A., Glattpark (Opfikon) (CH)

( * ) Notice: Subject to any disclaimer, the term of this patent is extended or adjusted under 35 U.S.C. 154(b) by 883 days.

(21) Appl. No.: 11/457,163

(22) Filed: Jul. 13, 2006

(65) Prior Publication Data
US 2007/0012893 A1    Jan. 18, 2007

Related U.S. Application Data

(60) Provisional application No. 60/699,048, filed on Jul. 13, 2005.

(51) Int. Cl.
*F16K 51/00*   (2006.01)
(52) U.S. Cl. .................................. 251/149.6; 251/149.1
(58) Field of Classification Search .............. 251/149.1, 251/149.3, 149.6, 149.7
See application file for complete search history.

(56) References Cited

U.S. PATENT DOCUMENTS

| | | | |
|---|---|---|---|
| 3,746,415 A | 7/1973 | Thomson | |
| 4,012,478 A | 3/1977 | Horikawa et al. | |
| 4,093,578 A | 6/1978 | Vasiliev et al. | |
| 4,970,010 A | 11/1990 | Erickson et al. | |
| 5,549,577 A * | 8/1996 | Siegel et al. | 604/256 |
| 5,639,810 A | 6/1997 | Smith, III et al. | |
| 6,120,536 A * | 9/2000 | Ding et al. | 623/1.43 |
| 6,291,063 B1 | 9/2001 | Shah et al. | |
| 6,379,507 B1 * | 4/2002 | Satoh et al. | 203/29 |
| 6,406,030 B1 | 6/2002 | Fang et al. | |

(Continued)

FOREIGN PATENT DOCUMENTS

WO    WO 99/32168 A1    7/1999

(Continued)

OTHER PUBLICATIONS

DOW Corning Brand Plastics Additives Selector Guide; Received Nov. 21, 2003.

*Primary Examiner*—John K Fristoe, Jr.
(74) *Attorney, Agent, or Firm*—Marshall, Gerstein & Borun LLP

(57) ABSTRACT

An elastomeric gland is provided for a luer activating device (LAD). and comprises a unique lubricant and/or wetting agent and/or anti-clotting agent incorporated into the elastomer gland during raw material formulation, calendar blending/molding/curing to deliver the surface lubricity and/or wettability and/or avoid slit plane re-knitting and/or gland induced valve stick down of such devices Functional additive chemistries are selected in terms of generated functional performance level, thermal stability against processing, molecular migratability, molecular weight and elastomer substrate of interest. These additives could include lubricants like chemically modified silicone oils and/or wetting agents like silicone-based surfactant. Elastomer gland with wetting agent would ease fluid path priming and minimize micro air bubble adherence to gland surface. Additives may also include anti-clotting agents intended to reduce potential for clot formation within the fluid path and interstitial space of the valve during blood sampling and infusion.

8 Claims, 1 Drawing Sheet

U.S. PATENT DOCUMENTS

| | | | |
|---|---|---|---|
| 6,595,964 B2 * | 7/2003 | Finley et al. | 604/246 |
| 6,723,439 B2 * | 4/2004 | Amidaiji et al. | 428/447 |
| 6,866,656 B2 | 3/2005 | Tingey et al. | |
| 6,871,838 B2 * | 3/2005 | Raines et al. | 251/149.4 |
| 6,887,270 B2 * | 5/2005 | Miller et al. | 623/11.11 |
| 2006/0129225 A1 * | 6/2006 | Kopia et al. | 623/1.13 |
| 2007/0073246 A1 * | 3/2007 | Simon | 604/246 |

FOREIGN PATENT DOCUMENTS

| | | |
|---|---|---|
| WO | WO 99/44755 A1 | 9/1999 |
| WO | WO 01/90230 A1 | 11/2001 |

* cited by examiner

_U.S. Patent_    Dec. 28, 2010    US 7,857,285 B2

LUBRICIOUS OR/AND WETTABLE OR/AND ANTI-THROMBIN ELASTOMERIC GLAND MATERIALS IN LUER ACTIVATED DEVICES

This application claims the benefit of U.S. Provisional Application Ser. No. 60/699,048 filed on Jul. 13, 2005

BACKGROUND OF THE INVENTION

Luer activated devices or LADs are designed to provide needleless aseptic access to medical fluid flow systems such as intravenous fluid administration sets or lines typically used in healthcare. LADs eliminate the need for "sharp" needles or blunt plastic cannula of specialized shape. Many of these LADs utilize elastomeric boots or glands which are displaced or deformed in some manner when a standard male luer tip is inserted into the device. This displacement or deformation will generally open a flow path through the device. In some designs, the gland will operate in conjunction with other components of the device to establish this flow path. After the luer tip is removed, the gland recovers to shut off the flow path.

In many LAD designs the flow path is established by the opening of a pre-formed slit or orifice in the gland when the gland is deformed or displaced. A portion of the flow path then extends through the orifice. When the male luer tip is withdrawn, the gland recovers to its starting condition causing the slit or orifice to close, shutting off the flow path. One type of luer activated device is described in more detail in U.S. Pat. No. 6,039,302 which is incorporated herein by reference.

LADs must be capable of multiple accesses by the luer tip. To do so, the gland must be able to recover to a closed position upon removal of the luer tip and then be capable of actuation by the next insertion of the luer tip. Moreover, if the gland utilizes a pre-formed slit or orifice opening, this opening must remain capable of being repeatedly opened by the insertion of the luer tip and closing after the luer tip is removed.

Lubrication plays a critical role in ensuring gland opening and return consistency over service life. In addition, the lubricant may act as a shield or coating which prevents slit or orifice re-knit, i.e. knitting shut, such that the slit or orifice doesn't open properly upon insertion of the luer tip.

Conventional surface lubrication has been applied to the web area of the gland to prevent valve stick down which may otherwise prevent the gland from returning to its starting position and closing the slit and has also been applied to the slit or orifice to ensure consistent slit plane opening and minimize the potential for silicone molecular cross-linking or re-knit. Typically, lubricant is applied to the gland just prior to assembly of the luer activated device. Too much or too little application of lubricant can interfere with valve operation during use and may result in valve failure. In addition, if the manufacturing process does not adequately apply or incorrectly applies the lubricant, re-knit may occur resulting in the slit failing to open on first use, the gland may stick down and fail to recover after actuation or the slit may later reseal and/or re-knit. In addition, sterilization via gamma irradiation may facilitate the re-knitting process. To ensure product robustness, in process inspection may be used which creates a major logistical bottle-neck to the manufacturing process flow.

In addition, the hydrophobic nature of the gland sometimes causes small or micro air bubbles to form on the gland when aqueous fluids are made to flow through the LAD such as when the LAD is primed with saline. The hydrophobic nature of the gland also occasionally prevents adequate priming of the LAD.

Another area of possible concern can be with the use of LADs in blood fluid transfer. The natural tendency of blood to clot can result in blockage of the flow path in LADs.

It would be desirable to provide a LAD that has a gland that includes a lubricant incorporated into the gland itself which could prevent gland stick down or slit/orifice re-knit.

It would also be desirable to incorporate other agents such as wetting agents or surfactants to prevent the micro bubble formation and allow proper priming. It would also be advantageous to incorporate anti-clotting agents to prevent clotting when the LAD is used with blood or blood components.

SUMMARY OF THE INVENTION

In one aspect of the present invention, a unique lubricant and/or wetting agent and/or anti-clotting agent is incorporated into an elastomeric gland of a Luer Activated Device (LAD) during raw material formulation, calendar blending/molding/curing. Such agent delivers surface lubricity and avoid slit plane re-knitting or gland web induced valve stick down and/or to increase wettability of the gland and/or to prevent clotting in the fluid path and interstitial spaces.

In another aspect of the present invention, an elastomeric gland having a lubricant incorporated therein is provided.

In yet another aspect of the present invention, an elastomeric gland having a wetting agent incorporated therein is provided.

In yet another aspect of the present invention, an elastomeric gland having a an anti-clotting agent incorporated therein is provided.

In yet another aspect of the present invention, an elastomeric gland having a lubricant, wetting agent and anticlotting agent incorporated therein is provided.

In yet another aspect of the present invention, a luer activated device including an elastomeric gland having one or more of a lubricant, wetting agent and anti-clotting agent incorporated therein is provided.

In yet another aspect of the present invention, a method of making an elastomeric gland including the steps of mixing one or more of lubricant, wetting agent and anti-clotting agent with a elastomeric material to form an additive enhanced elastomeric material, molding the additive enhanced elastomeric material into a gland, and curing the additive enhanced elastomeric material is provided.

Other aspects, objects and advantages of the present invention will be understood from the following description according to the preferred embodiments of the present invention, specifically including stated and unstated combinations of the various features which are described herein and relevant information which is shown in the accompanying drawings and examples.

BRIEF DESCRIPTION OF THE DRAWINGS

In describing the various aspects of the present invention, reference will be made to the accompanying drawing, wherein.

DETAILED DESCRIPTION OF THE INVENTION

Figure 1:
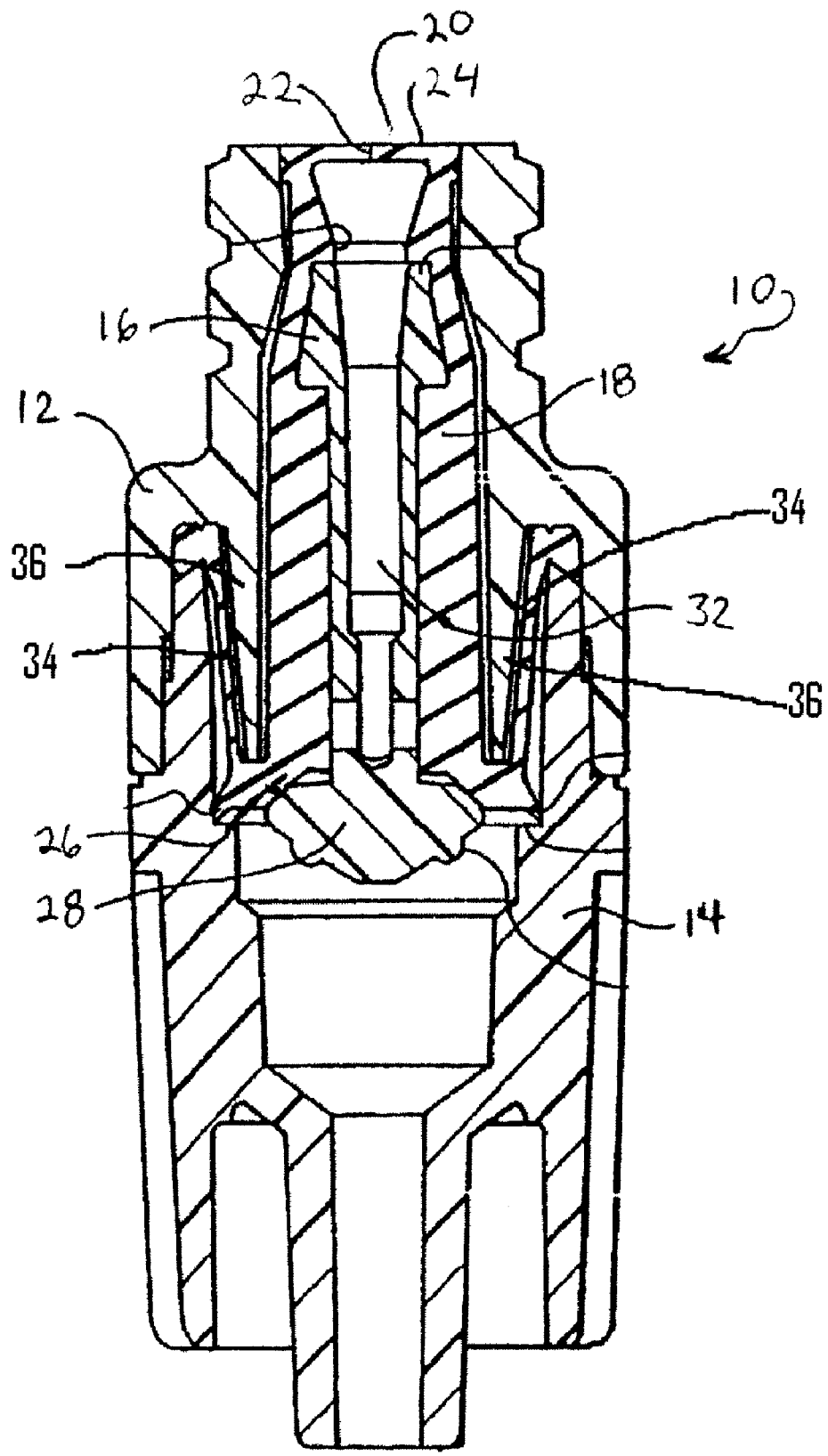
FIG. 1 is a side sectional view of a luer activating device or valve including a gland composed of a preferred embodiment of the invention.

Referring to FIG. 1, a typical luer activating device ("LAD") or valve 10 is shown. The LAD 10 comprises four main components: inlet housing 12, outlet housing 14, center post 16 and gland 18. The center post 16 and the gland 18 form the "working valve". The inlet and outlet housings 12, 14 serve to physically retain these two working components. When a luer tip (not shown) is attached to the top silicone surface 20 of the gland and advanced, it pushes the gland downward, opening a proximal slit 22 at gland top 24 and eventually opening a distal (second) seal 26 between the bulbous end 28 of the center post and the base of the gland. This creates a continuous fluid path 32 through the device. Removal of the actuating male luer reverses this process thereby closing the valve. At rest, the LAD 10 resides in the fully closed, swab-able position.

Lubrication is typically applied to the web area 34 between the inner ring 36 of inlet housing 12 and to slit 22. This extra step in the manufacturing process creates inefficiencies and raises the possibility of introducing future failing of the LAD.

In the preferred embodiment a unique lubricant and/or wetting agent and/or anti-clotting agent is incorporated into an elastomeric gland of an LAD during raw material formulation, calendar blending/molding/curing to deliver the surface lubricity and/or wettability and/or anti-clotting ability. The incorporated lubricant reduces or avoids slit plane re-knitting or gland web induced valve stick down, the wetting agent reduces or prevents micro air bubble formation and improves wettability or priming, and the anti-clotting agent reduces or prevents blood clotting within the fluid path and interstitial space during blood sampling and infusion.

In addition to the functional benefits mentioned above, additives such as these dramatically simplify the valve assembly process and current controls necessary to meter precise lubricant application weight to particular zones within the valve geometry.

Functional additive chemistries are selected in terms of generated functional performance level, thermal stability against processing, molecular migratability, molecular weight and elastomer substrate of interest. These additives can include lubricant like chemically modified silicone oils and/or wetting agent like silicone-based surfactant. Additives may also include anti-clotting agents such anti-platelet, anti-fibrin, anti-coagulant agents and/or direct thrombin inhibitors. These anti-clotting agents reduce potential for clot formation within the fluid path and interstitial space of the valve during blood sampling and infusion.

In alternate embodiments a wide variety of additives such as lubricants, wetting agents or anti-clotting compounds can be homogeneously blended into the silicone elastomer formulations thereby embedding a permanent supply of these materials in the gland which have the pre-disposition to bloom to the surface at some predictable level throughout the service life of the valve.

Additive blooms toward the elastomer surface over time after blending/molding/curing of elastomer and additives. These blooming kinetics dictating elastomer surface properties over time are controlled by additive molecular size, additive loadings, environmental temperature and elastomer substrate chemistry. Additive loading is usually low (often <5 wt %) to yield needed functional performance while not compromising material mechanical properties to fulfill other needed device functions.

In preferred embodiments, all additives of lubricant, wetting agent and/or anti-clotting agent will be mixed into elastomer matrix during calendaring & blending, followed with molding/curing.

Additive loading in elastomer typically varies from 0.1 to 5 wt %. In a preferred embodiment the additives compounded into the elastomeric material of the gland can include one or more of the following:

(1) 0.1-5 wt % of one or more lubricants;
(2) 0.1-5 wt % of one or more wetting agents; and
(3) 0.1-5 wt % of one or more anti-clotting agents.

Lubricant additive chemistry can include one or more of fatty amides, metallic stearates, waxes, esters, silicone and process oil and blends/chemical derivatives thereof, The lubricant(s) can be a fluorinated silicone oil and/or a phenyl modified silicone oil. The fluorinated silicone oil and/or phenyl modified silicone may have a viscosity of 1000 centistokes (cs) or less, 500 cs or less and/or 200 cs or less. Fluorinated silicone oils can include dimethyl, methyl trifluoropropyl siloxane which is commercially available under the trade name FL-100 (100 cs) through Shin Etsu and methyl trifluoropropyl siloxane which is commercially available under the trade name MED 400 (1000 cs) through Nusil. Phenyl modified silicone oil can include dimethyl, phenylmethyl siloxane which is commercially available under the trade name DC550 (125 cs) through Dow Corning.

The lubricant(s) in total can be added from about 0.1 to about 5% by weight of the elastomeric substrate. In one embodiment, the total amount of lubricant(s) added can be from about 1 to about 3% by weight of the elastomeric substrate.

Wetting agent chemistry can include one or more surfactants like sorbitan ester, ethoxylated fatty alcohol, silicone-based and hydrophilic polymers such as PEO and blends/chemical derivatives thereof. The wetting agent can have a viscosity of 500 cs or less, 100 cs or less and/or 25 cs or less. Silicone polyether copolymers can include Silwet L-77 (20 cs) commercially available through GE and DC5324 (350 cs) and DC193 (335 cs) commercially available through Dow Corning.

The wetting agent(s) in total can be added from about 0.1 to about 5% by weight of the elastomeric substrate. In one embodiment, the total amount of wetting agent(s) added can be from about 1 to about 3% by weight of the elastomeric substrate.

Anti-clotting additive chemistry can include one or more of an anti-platelet, anti-coagulant agents and direct thrombin inhibitor, preferably 1-3 wt % of heparin sodium (sodium salt of mucopolysaccharide).

The present invention is not limited to silicone based glands. Elastomer substrates for additive impregnation can encompass, and are not limited to, silicone, polyisoprene, butyl, styrene-butadiene rubber, thermoplastic elastomers (TPE) and blends of two or more polymer components listed above. Physical forms of additive could be powder, bead, pellet or liquid depending on process/condition/equipment used and product requirement. Molding methods for elastomer/additive system could include injection, compression, and transfer molding.

EXAMPLE 1

In order to determine the functional attributes of the additive enhanced glands, a number of plaques of an elastomeric substrate typically used in making glands of LADs were made incorporating one or more additives along with a control having no additive.

The following table identifies the additives and testing performed:

| Mix # | Additives | % by weight | # of plaques to make | C.O.F vs. Time | Wetting contact angle | Blood Clotting Tendency | Tensile bar testing after gamma | Material re-knit |
|---|---|---|---|---|---|---|---|---|
| 1 | No Additives/Control Group | 0.0 | 5 | X | X | X | X | X |
| 2 | FL-100 fluorosilicone (100 cs) | 3.0 | 4 | X | | | X | X |
| 3 | DC550 phenyl silicone (125 cs) | 3.0 | 4 | X | | | X | X |
| 4 | MED 400 fluorosilicone (1000 cs) | 1.0 | 2 | X | | | | X |
| 5 | MED 400 fluorosilicone (1000 cs) | 3.0 | 4 | X | | | X | X |
| 6 | MED 400 fluorosilicone (1000 cs) | 5.0 | 4 | X | | | X | X |
| 7 | L-77 polysiloxane polyether copolymer (20 cs) | 1.0 | 2 | | X | | | |
| 8 | L-77 polysiloxane polyether copolymer (20 cs) | 3.0 | 5 | X | X | X | X | |
| 9 | DC5324 polysiloxane polyether copolymer (350 cs) | 1.0 | 2 | | X | | | |
| 10 | DC5324 polysiloxane polyether copolymer (350 cs) | 3.0 | 5 | X | X | X | X | |
| 11 | DC193 polysiloxane polyether copolymer (335 cs) | 1.0 | 2 | | X | | | |
| 12 | DC193 polysiloxane polyether copolymer (335 cs) | 3.0 | 5 | X | X | X | X | |
| 13 | Heparin sodium salt | 1.0 | 2 | | | X | | |
| 14 | Heparin sodium salt | 3.0 | 3 | | | X | X | |
| 15 | Heparin sodium salt | 5.0 | 3 | | | X | X | |
| 16 | MED 400 fluorosilicone (1000 cs) and L-77 wetting agent | 1.0 of each | 5 | X | X | | X | X |
| 17 | MED 400 fluorosilicone (1000 cs) and L-77 wetting agent and heparin sodium salt | 1.0 of each | 5 | X | X | X | X | X |

The additives were mixed to Wacker Elastosil R4000/50 silicone substrate material in above-shown amounts. All samples were formed into 6 inch by 6 inch by ⅛ inch transfer molds with no post-curing.

The presence and/or extent of lubricant blooming to the surface of the substrate should be confirmed by performing Coefficient of Friction (COF) testing over several time intervals. The COF testing was carried out on all the mixes except for mixes 7, 9, 11 and 13-15.

Coefficient of Friction is the ratio of the frictional force to the gravitational force acting perpendicular to the two surfaces in contact. The coefficient of friction is a measure of the resistance to moving an object across a surface. A frictional force is the resisting force when a surface slides over another substance. Static friction is the force to start the sled in motion from rest. Kinetic friction is the force to keep the sled moving. Contact Substrate is the material attached to the friction table or the friction sled that the testing material slides across.

Testing was performed at four different times for each mix that underwent COF testing as follows:
Time interval 1=between 1 and 4 hours after being molded
Time interval 2=24±4 hours after being molded
Time interval 3=168 hours (7 days)±24 hours after being molded
Time interval 4=between 2-3 weeks after being molded (between 336 and 504 hours)

Testing was performed on n=5 samples for each mix at each different time interval. The same sample was not tested more than once.

Each sample was cut to a 1.5 inch×2.0 inch rectangle from its plaque immediately before testing. Each sample was cut with a razor blade or other suitably sharp instrument. No threads, visible particulate, etc should be present on each sample after cutting that may interfere with the sliding surface of the sample. Also, care was taken not to touch, if possible, the sliding surface of the sample, since lubrication may be wiped away.

Each sample was attached to the bottom of the sled of the friction fixture of the Instron 5565, serial no. c1187. Also, the stationary surface on which the sled moves was comprised of a silver-gray fiberglass screening mesh in order to prevent silicone skipping.

The Instron 5565 was set to pull at 20 inches per minute and the sled carried a 20 pound capacity load cell. Once the frictional force measurements have been taken, the weight of the sled and sample are entered into the Instron Series IX software, both static and kinetic coefficients of friction values were calculated.

The results of the COF testing are shown in the tables below:

|  | Mix # 1 | | | | | | | | Mix # 2 | | | | | | | |
| --- | --- | --- | --- | --- | --- | --- | --- | --- | --- | --- | --- | --- | --- | --- | --- | --- |
|  | 1–4 hours | | 24 ± 4 hours | | 168 ± 24 hrs | | 336~504 hrs | | 1–4 hours | | 24 ± 4 hours | | 168 ± 24 hrs | | 336~504 hrs | |
|  | Static | Kinetic | Static | Kinetic | Static | Kinetic | Static | Kinetic | Static | Kinetic | Static | Kinetic | Static | Kinetic | Static | Kinetic |
| Mean | 0.742 | 0.620 | 0.779 | 0.494 | 0.635 | 0.461 | 0.698 | 0.414 | 0.719 | 0.582 | 0.601 | 0.447 | 0.490 | 0.218 | 0.447 | 0.197 |
| S.D. | 0.036 | 0.031 | 0.053 | 0.027 | 0.017 | 0.029 | 0.059 | 0.027 | 0.054 | 0.043 | 0.069 | 0.065 | 0.082 | 0.034 | 0.038 | 0.028 |

|  | Mix # 3 | | | | | | | | Mix # 4 | | | | | | | |
| --- | --- | --- | --- | --- | --- | --- | --- | --- | --- | --- | --- | --- | --- | --- | --- | --- |
|  | 1–4 hours | | 24 ± 4 hours | | 168 ± 24 hrs | | 336~504 hrs | | 1–4 hours | | 24 ± 4 hours | | 168 ± 24 hrs | | 336~504 hrs | |
|  | Static | Kinetic | Static | Kinetic | Static | Kinetic | Static | Kinetic | Static | Kinetic | Static | Kinetic | Static | Kinetic | Static | Kinetic |
| Mean | 0.467 | 0.342 | 0.457 | 0.181 | 0.411 | 0.083 | 0.442 | 0.113 | 0.860 | 0.458 | 0.660 | 0.460 | 0.572 | 0.375 | 0.890 | 0.445 |
| S.D. | 0.042 | 0.048 | 0.030 | 0.023 | 0.045 | 0.015 | 0.025 | 0.017 | 0.038 | 0.028 | 0.040 | 0.029 | 0.024 | 0.013 | 0.074 | 0.062 |

|  | Mix # 5 | | | | | | | | Mix # 6 | | | | | | | |
| --- | --- | --- | --- | --- | --- | --- | --- | --- | --- | --- | --- | --- | --- | --- | --- | --- |
|  | 1–4 hours | | 24 ± 4 hours | | 168 ± 24 hrs | | 336~504 hrs | | 1–4 hours | | 24 ± 4 hours | | 168 ± 24 hrs | | 336~504 hrs | |
|  | Static | Kinetic | Static | Kinetic | Static | Kinetic | Static | Kinetic | Static | Kinetic | Static | Kinetic | Static | Kinetic | Static | Kinetic |
| Mean | 0.648 | 0.394 | 0.698 | 0.472 | 0.634 | 0.423 | 0.618 | 0.407 | 0.717 | 0.647 | 0.794 | 0.620 | 0.697 | 0.626 | 0.870 | 0.615 |
| S.D. | 0.062 | 0.054 | 0.046 | 0.031 | 0.017 | 0.013 | 0.045 | 0.029 | 0.010 | 0.036 | 0.050 | 0.051 | 0.028 | 0.025 | 0.036 | 0.019 |

|  | Mix # 8 | | | | | | | | Mix # 10 | | | | | | | |
| --- | --- | --- | --- | --- | --- | --- | --- | --- | --- | --- | --- | --- | --- | --- | --- | --- |
|  | 1–4 hours | | 24 ± 4 hours | | 168 ± 24 hrs | | 336~504 hrs | | 1–4 hours | | 24 ± 4 hours | | 168 ± 24 hrs | | 336~504 hrs | |
|  | Static | Kinetic | Static | Kinetic | Static | Kinetic | Static | Kinetic | Static | Kinetic | Static | Kinetic | Static | Kinetic | Static | Kinetic |
| Mean | 0.814 | 0.342 | 0.775 | 0.202 | 0.782 | 0.124 | 0.761 | 0.110 | 0.922 | 0.539 | 1.070 | 0.525 | 0.959 | 0.471 | 0.981 | 0.529 |
| S.D. | 0.111 | 0.095 | 0.098 | 0.054 | 0.062 | 0.016 | 0.098 | 0.055 | 0.073 | 0.034 | 0.158 | 0.030 | 0.060 | 0.027 | 0.054 | 0.039 |

|  | Mix # 12 | | | | | | | | Mix # 16 | | | | | | | |
| --- | --- | --- | --- | --- | --- | --- | --- | --- | --- | --- | --- | --- | --- | --- | --- | --- |
|  | 1–4 hours | | 24 ± 4 hours | | 168 ± 24 hrs | | 336~504 hrs | | 1–4 hours | | 24 ± 4 hours | | 168 ± 24 hrs | | 336~504 hrs | |
|  | Static | Kinetic | Static | Kinetic | Static | Kinetic | Static | Kinetic | Static | Kinetic | Static | Kinetic | Static | Kinetic | Static | Kinetic |
| Mean | 1.159 | 0.600 | 0.885 | 0.613 | 0.997 | 0.532 | 0.827 | 0.433 | 1.152 | 0.553 | 1.306 | 0.597 | 1.243 | 0.635 | 1.149 | 0.566 |
| S.D. | 0.185 | 0.063 | 0.076 | 0.028 | 0.140 | 0.050 | 0.122 | 0.016 | 0.069 | 0.035 | 0.094 | 0.009 | 0.110 | 0.051 | 0.146 | 0.075 |

|  | Mix # 17 | | | | | | | |
| --- | --- | --- | --- | --- | --- | --- | --- | --- |
|  | 1–4 hours | | 24 ± 4 hours | | 168 ± 24 hrs | | 336~504 hrs | |
|  | Static | Kinetic | Static | Kinetic | Static | Kinetic | Static | Kinetic |
| Mean | 1.069 | 0.573 | 1.220 | 0.615 | 0.812 | 0.508 | 0.926 | 0.551 |
| S.D. | 0.046 | 0.024 | 0.113 | 0.023 | 0.081 | 0.015 | 0.103 | 0.036 |

EXAMPLE 2

Some of the mixes of Example 1, specifically mixes 1-7, 16 and 17 were also tested to determine the effect of the lubricant additive on molecular cross-linking or re-knit of the silicone substrate.

For each mix tested, six rectangles were cut from the plaque with each rectangle measuring 3 inch×1 inch. Two of the rectangular samples were stacked together, so that a double-thick 3 inch×1 inch sample is formed. Wax paper was placed between the last 1 inch×1 inch end of the joined double-thick rectangle, so that only two-thirds of the area of each sample was in contact with each other. This was repeated for all n=6 rectangles in each group, so that n=3 samples were created for each group.

These samples were then placed into a fixture that helped to ensure a constant compressive force through sterilization. This fixture cannot contain any metal due to the gamma irradiation processing. This force should be about 5 psi, or 15 pounds per sample, distributed as evenly as possible on the sample surface.

Once placed into their fixtures, the samples (with fixtures) were each subjected to 41-61 kGy gamma irradiation, which is higher than the typical sterilization dosage. This is intended to induce molecular cross-linking of the silicone samples. The samples were under compression for about fifteen days.

Once the fifteen days of compression and irradiation were complete, each sample was removed from its fixture. The wax paper was also removed from each sample. The two loose flaps of the sample are placed in the jaw fixtures of a calibrated tensile tester or a force measuring instrument such as the Instron 5565 which was used for this test. The sample was peeled apart using 20 inches per minute as a crosshead speed. The procedure was repeated for all the remaining samples. The highest peal force and elongation to complete the peal for each sample was recorded. The mean and standard deviation of these values were calculated for each mix.

The results of the re-knit testing is shown in the tables below:

|  | Peal Force (lbf) | Elongation (in) | Observation |  |  |  |  |  |
|---|---|---|---|---|---|---|---|---|
| Mix # 1 | 6.175 | 4.189 | sep | Peal Force (lbf) | | Elongation (in) | |
| Mix # 1 | 5.299 | 3.919 | sep | Mean | Std Dev | Mean | Std Dev |
| Mix # 1 | 7.454 | 4.178 | sep | 6.309 | 1.0838 | 4.095 | 0.1528 |
| Mix # 2 | 4.415 | 4.024 | sep | Peal Force (lbf) | | Elongation (in) | |
| Mix # 2 | 3.473 | 3.707 | sep | Mean | Std Dev | Mean | Std Dev |
| Mix # 2 | 4.46 | 4.042 | sep | 4.116 | 0.5573 | 3.924 | 0.1884 |
| Mix # 3 | 5.387 | 4.516 | sep | Peal Force (lbf) | | Elongation (in) | |
| Mix # 3 | 5.237 | 4.214 | sep | Mean | Std Dev | Mean | Std Dev |
| Mix # 3 | 4.712 | 4.046 | sep | 5.112 | 0.3544 | 4.269 | 0.2382 |
| Mix # 4 | 9.781 | 4.546 | sep | | | | |
| Mix # 5 | 6.152 | 4.662 | sep | Peal Force (lbf) | | Elongation (in) | |
| Mix # 5 | 6.844 | 4.622 | sep | Mean | Std Dev | Mean | Std Dev |
| Mix # 5 | 6.945 | 4.447 | sep | 6.647 | 0.4316 | 4.577 | 0.1143 |
| Mix # 6 | 5.671 | 4.261 | sep | Peal Force (lbf) | | Elongation (in) | |
| Mix # 6 | 6.871 | 4.324 | sep | Mean | Std Dev | Mean | Std Dev |
| Mix # 6 | 6.544 | 4.006 | sep | 6.362 | 0.6204 | 4.197 | 0.1684 |
| Mix # 7 | 27.409 | 1.218 | tear | Peal Force (lbf) | | Elongation (in) | |
| Mix # 7 | 28.194 | 3.246 | tear | Mean | Std Dev | Mean | Std Dev |
| N/A | N/A | N/A | N/A | 27.802 | 0.5551 | 2.232 | 1.434 |
| Mix # 16 | 26.395 | 2.587 | tear | Peal Force (lbf) | | Elongation (in) | |
| Mix # 16 | 25.395 | 2.136 | tear | Mean | Std Dev | Mean | Std Dev |
| Mix # 16 | 23.599 | 1.806 | tear | 25.13 | 1.4168 | 2.176 | 0.3921 |
| Mix # 17 | 26.423 | 1.990 | tear | Peal Force (lbf) | | Elongation (in) | |
| Mix # 17 | 27.063 | 2.998 | tear | Mean | Std Dev | Mean | Std Dev |
| Mix # 17 | 26.498 | 2.630 | tear | 26.661 | 0.3499 | 2.539 | 0.5101 |

Tear - denotes a sample where the two pieces of material tore rather than separated from one another when pulled apart
Sep - denotes a sample where the two pieces of material separated when pulled apart

EXAMPLE 3

Several of mixes of Example 1 were tested to determine the presence and/or extent of the wetting agent on the surface of the substrate. Contact angle wetting test was performed on mixes 1, 7-12, 16 and 17. Water droplet contact angles were measured using an AST VCA Optima contact angle goniometer. Five droplets were measured in three locations on the test plaque for each mixture. Each plaque was divided into nine symmetric sections resembling a tic-tac-toe grid and the top right most, center, and bottom left most sections were used as the test locations.

Five droplets, each having a volume of 2.0 ul, were dispensed linearly across the top half of each section. A measurement was taken after the each droplet was deposited with a short time lag to ensure no droplet movement. The measurements were repeated after a minimum of 24 hours of open exposure in a laboratory hood.

The results of the water droplet contact angle testing is shown on the following table:

| | Contact Angle, degrees | | | | | |
|---|---|---|---|---|---|---|
| | Test | | | | | |
| Mix | 1 | 2 | Average | STD[1] | CV[2] (%) | N[3] |
| 1 | 97.6 | 108.7 | 102.4 | 12.9 | 12.6 | 70 |
| 7 | 38.0 | 33.7 | 35.9 | 4.3 | 11.9 | 62 |
| 8 | 20.0 | 21.5 | 20.8 | 2.7 | 13.1 | 60 |
| 9 | 105.7 | 112.0 | 108.7 | 15.1 | 13.9 | 62 |
| 10 | 113.4 | 112.7 | 113.0 | 2.2 | 1.9 | 60 |
| 11 | 113.4 | 113.9 | 113.7 | 2.7 | 2.4 | 60 |
| 12 | 111.2 | 111.4 | 111.3 | 2.7 | 2.5 | 60 |

-continued

| | Contact Angle, degrees | | | | | |
|---|---|---|---|---|---|---|
| | Test | | | | | |
| Mix | 1 | 2 | Average | STD[1] | CV[2] (%) | N[3] |
| 16 | 36.7 | 35.2 | 35.9 | 2.5 | 7.0 | 60 |
| 17 | 32.2 | 32.6 | 32.4 | 3.0 | 9.2 | 60 |

[1] STD = Standard deviation.
[2] CV = Coefficient of variation.
[3] N = number of measurements.

EXAMPLE 4

To determine the effect of the additives on the mechanical properties of the silicone substrate, tensile strength testing was performed on mixes 1-3, 5, 6, 8, 10, 12, and 14-17. Two different tensile test were performed: (1) stress and strain testing following the parameters set forth in ASTM D412 and (2) tear strength testing following the parameters set forth in ASTM D624.

For each test (stress/strain and tear strength), plaques from the mixes to be tested were first gamma-sterilized with a dose range of 18-38 kGy. For the stress/strain test, ASTM D412, Die C was used to cut n=5 samples. For the tear strength test, ASTM D624, Die B was used to cut n=5 samples. Foe each tensile test, each sample was secured in the calibrated tensile tester which for this test was an Instron 5565 and the crosshead speed was set a 20 inches per minute and sampling was set at 50 Hz for testing each sample For the stress/strain testing, the Instron Series IX software extrapolated the 100% modulus, 200% modulus, stress at break and elongation at break for each sample along with the mean and standard deviation for the group of n=5 samples.

For the tear strength testing, the Instron Series IX software extrapolated the force at break, stress at break, and elongation at break for each sample along with the mean and standard deviation for the group of n=5 samples.

The results of the testing are shown in the following tables:

| | | Tensile Test - Stress/Strain | | | | |
|---|---|---|---|---|---|---|
| Mix # | | 100% Modulus (psi) | 200% Modulus (psi) | Stress at Break (psi) | Elongation at Break (in) | Load at Break (lbf) |
| 1 | Mean | 105.862 | 81.972 | 1289.61 | 17.962 | 22.987 |
| | Std Dev | 3.988 | 2.502 | 291.889 | 1.994 | 5.203 |
| | Min | 99.319 | 79.143 | 911.032 | 15.222 | 16.239 |
| | Max | 109.139 | 84.862 | 1583.764 | 19.860 | 28.231 |
| 2 | Mean | 138.431 | 111.557 | 1267.062 | 13.519 | 22.585 |
| | Std Dev | 7.858 | 7.903 | 96.65 | 0.460 | 1.723 |
| | Min | 127.82 | 99.972 | 1136.886 | 13.073 | 20.265 |
| | Max | 146.064 | 117.531 | 1370.606 | 14.138 | 24.431 |
| 3 | Mean | 120.632 | 94.585 | 1241.529 | 16.01 | 22.130 |
| | Std Dev | 14.112 | 3.802 | 289.98 | 0.151 | 5.169 |
| | Min | 110.76 | 91.305 | 813.10 | 15.874 | 14.493 |
| | Max | 141.46 | 98.289 | 1444.54 | 16.187 | 25.749 |
| 5 | Mean | 107.11 | 78.833 | 1022.822 | 15.03 | 18.232 |
| | Std Dev | 4.234 | 7.993 | 443.231 | 6.656 | 7.901 |
| | Min | 102.767 | 67.87 | 433.03 | 5.106 | 7.719 |
| | Max | 111.455 | 86.85 | 1427.44 | 19.191 | 25.444 |
| 6 | Mean | 98.353 | 76.32 | 1247.73 | 19.132 | 22.241 |
| | Std Dev | 3.688 | 1.293 | 291.63 | .545 | 5.198 |
| | Min | 93.955 | 74.636 | 811.13 | 18.379 | 14.458 |
| | Max | 101.445 | 77.763 | 1414.79 | 19.665 | 25.219 |
| 8 | Mean | 84.163 | 62.446 | 1183.95 | 18.712 | 21.104 |
| | Std Dev | 5.704 | 10.537 | 244.8 | 0.795 | 4.364 |
| | Min | 76.776 | 50.464 | 759.23 | 17.819 | 13.533 |
| | Max | 91.032 | 72.652 | 1366.29 | 193.937 | 24.354 |
| 10 | Mean | 81.888 | 62.028 | 1337.06 | 20.624 | 23.833 |
| | Std Dev | 14.121 | 11.71 | 85.737 | 2.360 | 1.528 |
| | Min | 67.645 | 51.865 | 1241.6 | 18.069 | 22.132 |
| | Max | 102.232 | 78.224 | 1471.992 | 23.876 | 26.238 |
| 12 | Mean | 71.827 | 56.366 | 1292.92 | 21.182 | 23.046 |
| | Std Dev | 5.133 | 9.286 | 65.472 | 1.096 | 1.167 |
| | Min | 65.529 | 44.686 | 1199.66 | 20.218 | 21.384 |
| | Max | 76.658 | 66.373 | 1357.35 | 23.06 | 24.195 |
| 14 | Mean | 88.867 | 71.565 | 1159.114 | 18.067 | 20.661 |
| | Std Dev | 3.666 | 1.618 | 233.757 | .873 | 4.167 |
| | Min | 83.33 | 70.094 | 775.434 | 17.158 | 13.822 |
| | Max | 92.713 | 73.468 | 1414.286 | 19.427 | 25.210 |
| 15 | Mean | 84.834 | 66.559 | 1121.095 | 18.487 | 19.984 |
| | Std Dev | 9.208 | 11.293 | 213.832 | 1.543 | 3.812 |
| | Min | 74.083 | 56.689 | 747.535 | 16.909 | 13.325 |
| | Max | 97.852 | 82.75 | 1266.70 | 20.568 | 22.579 |
| 16 | Mean | 75.441 | 63.843 | 1163.06 | 21.22 | 20.732 |
| | Std Dev | 23.565 | 18.166 | 300.475 | 2.706 | 5.356 |
| | Min | 44.415 | 44.399 | 885.102 | 19.313 | 15.777 |
| | Max | 95.515 | 81.697 | 1577.311 | 25.735 | 28.116 |
| 17 | Mean | 91.186 | 73.303 | 1320.967 | 19.181 | 23.546 |
| | Std Dev | 5.294 | 3.184 | 218.36 | .774 | 3.892 |
| | Min | 85.457 | 70.747 | 936.445 | 18.267 | 16.692 |
| | Max | 99.546 | 78.083 | 1445.245 | 19.905 | 25.761 |

| | | Tensile Test - Tear Strength | | |
|---|---|---|---|---|
| Mix # | | Stress at Break (psi) | Elongation at Break (in) | Load at Break (lbf) |
| 1 | Mean | 489.561 | 7.738 | 15.176 |
| | Std Dev | 105.347 | 1.137 | 3.266 |
| | Min | 302.29 | 6.464 | 9.371 |
| | Max | 549.14 | 9.070 | 17.023 |
| 2 | Mean | 419.092 | 5.494 | 12.992 |
| | Std Dev | 72.767 | 0.260 | 2.256 |
| | Min | 337.866 | 5.141 | 10.474 |
| | Max | 511.454 | 5.769 | 15.855 |
| 3 | Mean | 442.621 | 5.422 | 13.721 |
| | Std Dev | 17.967 | 0.392 | 0.557 |
| | Min | 424.795 | 5.083 | 13.169 |
| | Max | 462.799 | 5.887 | 14.347 |
| 5 | Mean | 546.441 | 8.243 | 16.940 |
| | Std Dev | 122.698 | 2.504 | 3.804 |
| | Min | 419.44 | 5.543 | 13.003 |
| | Max | 679.417 | 10.733 | 21.062 |
| 6 | Mean | 430.215 | 7.027 | 13.337 |
| | Std Dev | 81.574 | 1.766 | 2.529 |
| | Min | 348.323 | 5.227 | 10.798 |
| | Max | 525.751 | 8.897 | 16.298 |
| 8 | Mean | 427.44 | 9.341 | 13.251 |
| | Std Dev | 32.069 | 1.400 | 0.994 |
| | Min | 385.512 | 8.350 | 11.951 |
| | Max | 458.294 | 11.647 | 14.207 |
| 10 | Mean | 412.567 | 8.632 | 12.790 |
| | Std Dev | 71.480 | 2.499 | 2.216 |
| | Min | 359.868 | 6.090 | 11.156 |
| | Max | 538.135 | 12.437 | 16.682 |

-continued

Tensile Test - Tear Strength

| Mix # | | Stress at Break (psi) | Elongation at Break (in) | Load at Break (lbf) |
|---|---|---|---|---|
| 12 | Mean | 505.815 | 10.887 | 15.680 |
| | Std Dev | 70.708 | 1.464 | 2.192 |
| | Min | 415.364 | 9.085 | 12.876 |
| | Max | 596.432 | 13.020 | 18.489 |
| 14 | Mean | 424.85 | 7.300 | 13.170 |
| | Std Dev | 23.529 | 0.384 | 0.729 |
| | Min | 406.662 | 6.740 | 12.607 |
| | Max | 465.969 | 7.690 | 14.445 |
| 15 | Mean | 414.465 | 7.899 | 12.848 |
| | Std Dev | 79.964 | 1.951 | 2.479 |
| | Min | 347.750 | 6.244 | 10.78 |
| | Max | 546.017 | 11.165 | 16.927 |
| 16 | Mean | 545.048 | 13.921 | 16.896 |
| | Std Dev | 39.656 | 1.125 | 1.229 |
| | Min | 489.512 | 12.217 | 15.175 |
| | Max | 597.886 | 15.277 | 18.534 |
| 17 | Mean | 465.039 | 8.267 | 14.416 |
| | Std Dev | 32.834 | 0.689 | 1.018 |
| | Min | 412.646 | 7.347 | 12.792 |
| | Max | 497.759 | 9.157 | 15.431 |

While the present invention has been described in detail with reference to the foregoing embodiments, other changes and modifications may still be made without departing from the scope of the present invention. It is understood that the present invention is not to be limited by the embodiments described herein. Indeed, the true measure of the scope of the present invention is defined by the appended claims including the full range of equivalents given to each element of each claim. Various features that are described herein can be used in any combination and are not limited to procure combinations that are specifically outlined herein.

The invention claimed is:

1. In a luer activated device including a housing having an inlet and an outlet and a gland attached to the housing, the gland comprising an elastomeric material, the elastomeric material being elastomeric silicone and having a plurality of additives selected from the group consisting of one or more lubricants, one or more wetting agents, and one or more anti-clotting agents incorporated in the elastomeric material sometime prior to release of the gland from a final molding step, the plurality of additives present at a total concentration of from about 0.1 to about 5% by weight of the elastomeric silicone, wherein the plurality of additives include:
   a) from about 1 to about 3% by weight of a fluorosilicone oil or a phenyl modified silicone oil;
   b) from about 1 to about 3% by weight of silicone polyether copolymer; and
   c) from about 1 to about 3% by weight of heparin sodium.

2. The gland of claim 1 wherein the one or more lubricants are selected from the group consisting of fluorosilicone oil having a viscosity of 500 cs or less, phenyl modified silicone oil having a viscosity of 500 cs or less and combinations thereof.

3. The gland of claim 1 wherein the one or more wetting agents are silicone polyether copolymers having a viscosity of 100 cs or less.

4. The gland of claim 1 wherein the one or more anti-clotting agents are heparin sodium salts.

5. A luer activated device comprising a housing adapted to accept a luer tip and a gland attached to the housing, said gland including an elastomeric material, the elastomeric material being elastomeric silicone, and a plurality of additives selected from the group consisting of at least one lubricant, at least one wetting agent, and at least one anti-clotting agent blended with the elastomeric material sometime prior to release of the gland from a final molding step, the plurality of additives present at a total concentration of from about 0.1 to about 5% by weight of the elastomeric silicone the plurality of additives include:
   a) from about 1 to about 3% by weight of a fluorosilicone oil or a phenyl modified silicone oil;
   b) from about 1 to about 3% by weight of silicone polyether copolymer; and
   c) from about 1 to about 3% by weight of heparin sodium.

6. The luer activated device of claim 5 wherein the at least one lubricant is selected from the group consisting of fluorosilicone oil having a viscosity of 500 cs or less, phenyl modified silicone oil having a viscosity of 500 cs or less and combinations thereof.

7. The luer activated device of claim 5 wherein the at least one wetting agent is a silicone polyether copolymer having a viscosity of 100 cs or less.

8. The luer activated device of claim 5 wherein the at least one anti-clotting agent is a heparin sodium salt.

* * * * *